United States Patent
Jacob

(10) Patent No.: US 11,146,211 B1
(45) Date of Patent: Oct. 12, 2021

(54) PHOTOVOLTAIC HORIZONTAL BEEHIVE SYSTEM

(71) Applicant: John B. Jacob, Rogue River, OR (US)

(72) Inventor: John B. Jacob, Rogue River, OR (US)

( * ) Notice: Subject to any disclaimer, the term of this patent is extended or adjusted under 35 U.S.C. 154(b) by 0 days.

(21) Appl. No.: 16/909,902

(22) Filed: Jun. 23, 2020

Related U.S. Application Data

(60) Provisional application No. 62/866,436, filed on Jun. 25, 2019.

(51) Int. Cl.
  *H02S 40/44* (2014.01)
  *A01K 47/00* (2006.01)
  *H02S 20/23* (2014.01)
  *H02S 20/30* (2014.01)
  *A01K 67/033* (2006.01)

(52) U.S. Cl.
  CPC .............. *H02S 40/44* (2014.12); *A01K 47/00* (2013.01); *A01K 67/033* (2013.01); *H02S 20/23* (2014.12); *H02S 20/30* (2014.12)

(58) Field of Classification Search
  None
  See application file for complete search history.

(56) References Cited

U.S. PATENT DOCUMENTS

| | | |
|---|---|---|
| 4,494,528 A | 1/1985 | Horton |
| 4,981,458 A * | 1/1991 | Johnston ................ A01K 49/00 449/32 |
| 5,575,703 A | 11/1996 | Stearns |
| 5,741,170 A * | 4/1998 | Orletsky ................ A01K 47/00 449/30 |
| 7,556,552 B1 | 7/2009 | Kemp et al. |
| 7,795,837 B1 | 9/2010 | Haun et al. |
| 8,152,590 B2 | 4/2012 | Brundage |
| 8,272,921 B2 | 9/2012 | Sinanis et al. |
| 9,041,338 B2 | 5/2015 | Shen et al. |
| 9,184,628 B2 | 11/2015 | Carpoff |

(Continued)

FOREIGN PATENT DOCUMENTS

CN  210671705 U  *  6/2020

OTHER PUBLICATIONS

English machine translation of Yuan (CN 210671705 U) provided by the EPO website. 2021. All Pages. (Year: 2021).*

Primary Examiner — Daniel P Malley, Jr.
(74) Attorney, Agent, or Firm — Jerry Haynes Law

(57) ABSTRACT

A photovoltaic horizontal beehive system provides a horizontal beehive. The brooder box has sidewalls and a floor wall that form an interior cavity. The cavity is segregated into independent compartments through a central fixed divider, and multiple removable dividers that segregate the brooder box into a queen bee colony and a honey bee colony. The removable dividers are manipulated in the cavity to adjust the size of each compartment to accommodate population changes in the bee colonies. A lid regulates access to the interior cavity. A solar panel operates on outer surface of lid. The solar panel harnesses sunlight to generate electricity used internally and externally of the brooder box. An electrical compartment in brooder box retains electrical components, like a battery, an inverter, and a charge controller. The solar-generated electricity is used internally for operation of an internal beehive apparatus, and carried distally to operate an external electrical apparatus.

19 Claims, 5 Drawing Sheets

(56) References Cited

U.S. PATENT DOCUMENTS

| | | |
|---|---|---|
| 9,246,035 B2 | 1/2016 | Eaton et al. |
| 9,332,739 B2 | 5/2016 | Al Khazim Al Ghamdi |
| 9,807,985 B2 | 11/2017 | Bulanyy |
| 9,812,896 B2 | 11/2017 | Imperial |
| 9,981,001 B2 | 5/2018 | Del Vecchio |
| 9,999,204 B2 | 6/2018 | Brunner |
| 2007/0218804 A1 | 9/2007 | Allan et al. |
| 2009/0288698 A1 | 11/2009 | Chen |
| 2013/0273808 A1* | 10/2013 | Al Khazim Al Ghamdi ............... A01K 47/06 449/13 |
| 2013/0298962 A1 | 11/2013 | Sorgento |
| 2016/0285304 A1 | 9/2016 | Stiefel |
| 2016/0301354 A1 | 10/2016 | Draffin et al. |
| 2017/0064931 A1* | 3/2017 | Tagliaferri ............. A01K 47/04 |
| 2017/0208779 A1* | 7/2017 | Rubright ................ A01K 47/02 |
| 2017/0360010 A1* | 12/2017 | Wilson-Rich .......... A01K 47/06 |
| 2018/0118340 A1* | 5/2018 | Russo .................... A01K 59/00 |
| 2018/0160656 A1 | 6/2018 | Ben-Shimon et al. |
| 2018/0287549 A1 | 10/2018 | Long et al. |
| 2018/0338476 A1* | 11/2018 | Richardson ............ A01K 47/06 |

\* cited by examiner

PHOTOVOLTAIC HORIZONTAL BEEHIVE SYSTEM

CROSS-REFERENCE TO RELATED APPLICATIONS

This application claims the benefits of U.S. provisional application No. 62/866,436, filed Jun. 25, 2019 and entitled RENEWABLE ENERGY SYSTEM FOR GENERATING ELECTRICITY AT A HORIZONTAL BEEHIVE FOR INTERNAL AND EXTERNAL CONSUMPTION, which provisional application is incorporated by reference herein in its entirety.

FIELD OF THE INVENTION

The present invention relates generally to a photovoltaic horizontal beehive system. The beehive system provides an elongated, horizontal beehive with a brooder box that can be segregated into multiple size-adjustable compartments that support both a queen bee colony and a honey production bee colony; and further includes a lid that regulates access to the colonies and supports a solar panel that generates electricity used both internally and externally of the brooder box; whereby the generated electricity is storable and regulated by a battery, an inverter, and a charge controller disposed in at least one of the compartments in the brooder box.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Typically, beekeeping is a known technique for producing honey and wax. Also, commercial pollination of agricultural products has also proved to benefit from bees and the honey they produce. Bees play a significant role in producing honey and wax. Bees produce these byproducts in a beehive, which is where the bees work, procreate, eat, and build honeycombs which have honey and wax therein. One such type of man-made beehive is a horizontal beehive. The horizontal beehive can be an elongated box with all the frames disposed at a single level. This allows a beekeeper to selectively access all the compartments in the frame.

Generally, a solar panel serves to absorb the solar radiation from the sun. Often, the solar panel includes a frame covered with a piece of glass or other transparent material. Solar radiation is transmitted through the glass and impinges heat absorptive surfaces to raise the temperature of those surfaces. In some instances, a fluid that is flowing near and through the solar panels absorbs the heat from these heated surfaces. Other times, the solar panel comprises photovoltaic cells that are excited by the heat, causing the creation of DC electricity. The DC current can be transmitted and/or converted to AC current for consumption. In other instances, the electricity generated by the solar panels is stored in a rechargeable battery for later use. The present invention works to generate, store, use, and transmit the solar power generated electricity directly at the beehive, which can include rural areas.

Other proposals have involved beehive systems that attempt to raise multiple types of bee colonies, while also accessing electricity in rural areas. The problem with these beehive systems is that they do not allow for both a queen bee and a worker bee to live together. Also, any electrical components requiring energy to operate, must access the energy from an outer source. Even though the above cited beehive systems meet some of the needs of the market, a photovoltaic horizontal beehive system that provides an elongated, horizontal beehive with a brooder box that can be segregated into multiple size-adjustable compartments that support, both a queen bee colony and a honey production bee colony; and further includes a lid that regulates access to the colonies and supports a solar panel that generates electricity used both, internally and externally of the brooder box; whereby the generated electricity is storable and regulated by a battery, an inverter, and a charge controller disposed in at least one of the compartments in the brooder box, is still desired.

SUMMARY

Illustrative embodiments of the disclosure are generally directed to a photovoltaic horizontal beehive system that provides an elongated, horizontal beehive that forms a brooder box for raising both queen bees and worker honey bees. The brooder box has sidewalls that form an interior cavity. The cavity is segregated into multiple size-adjustable compartments through use of at least one fixed divider, and multiple removable dividers that segregate the brooder box for supporting, both a queen bee colony and a honey production bee colony. The removable dividers are manipulated to change the size and shape of the compartments, so as to accommodate population changes in the bee colonies. The removable dividers can be manipulated in the cavity of the brooder box to adjust the size of each compartment. This can be useful for accommodating population changes in the queen bee and honey bee colonies. At least one electrical compartment is also formed from the removable dividers for retaining electrical components.

In some embodiments, the beehive system further includes a lid that is hingedly, detachably, or slidably operable on the sidewalls of the brooder box to regulate access to the interior cavity. The lid is defined by an outer surface and an inner surface. A solar panel is operable on the outer surface of the lid, lying parallel therewith. The solar panel harnesses sunlight to generate electricity that is used both, internally and externally of the brooder box.

In some embodiments, the beehive system further includes at least one electrical component, such as a battery, an inverter, and a charge controller for regulating the solar-generated electricity. The electrical components are disposed in the electrical compartment of the brooder box. The solar-generated electricity is used internally by an internal brooder box apparatus; and transmitted externally to an external electrical apparatus for bee monitoring and maintenance functions, power tool electricity source solutions, surplus power supply to the energy market, and general rural energy needs.

One aspect of a photovoltaic horizontal beehive system comprises a brooder box having a floor wall and multiple sidewalls forming an interior cavity, the sidewalls being defined by at least one bee passageway enabling passage between the interior cavity and the exterior of the brooder box.

The beehive system also comprises a lid disposed on the sidewalls of the brooder box, the lid being operable to move between an open position and a closed position to regulate access to the interior cavity of the brooder box, the lid being defined by an outer surface and an inner surface.

The beehive system also comprises at least one removable divider operable to segregate the interior cavity of the brooder box into multiple compartments, the removable divider being disposed substantially parallel with the sidewalls and perpendicular with the floor wall, the removable divider further being operable to reposition in the interior cavity, whereby the size and dimension of the compartments is adjustable.

The beehive system also comprises a solar panel disposed on the outer surface of the lid, the solar panel being operable to harness sunlight for generating electricity.

The beehive system also comprises one or more electrical components operatively connected to the solar panel, the electrical components operable to regulate the generated electricity, the electrical components disposed in at least one of the compartments of the brooder box; whereby the electricity is regulated for powering an internal brooder box apparatus in, or proximal to the brooder box; whereby the electricity is regulated for powering an external electrical apparatus disposed distally from the brooder box.

In another aspect, the brooder box is defined by a rectangular shape.

In another aspect, the brooder box comprises a horizontal beehive.

In another aspect, the sidewalls are about 65" long and 28" high.

In another aspect, the system further comprises a fixed central divider disposed substantially parallel with the sidewalls and perpendicular with the floor wall.

In another aspect, the fixed central divider traversing centrally across the interior cavity.

In another aspect, the sidewalls comprise a rail for slidably guiding the removable divider.

In another aspect, the lid comprises a hinge.

In another aspect, the lid is hingedly attached to one of the sidewalls of the brooder box.

In another aspect, each compartment is in communication with a bee passageway.

In another aspect, the solar panel comprises multiple photovoltaic cells.

In another aspect, the compartments comprise a queen bee colony compartment, a honey bee colony compartment, and an electrical component compartment.

In another aspect, the electrical components include at least one of the following: a battery, an inverter, a charge controller, and an electrical cable.

In another aspect, the inverter is operatively connected to the solar panel, and operable to convert a direct current generated by the solar panel to an alternating current.

In another aspect, the charge controller is operatively connected to the solar panel, and operable to limit the rate of electrical current flowing from the solar panel.

In another aspect, the internal brooder box apparatus includes at least one of the following: a light source, a cooling component for cooling the interior cavity of the brooder box, and an electrical mite exterminator.

In another aspect, the external electrical apparatus includes at least one of the following: an electrical fence, a data gathering device, and a generator.

One objective of the present invention is to provide a horizontal beehive that provides the dual function of brooding bee colonies and generating electricity through solar power.

Another objective is to simultaneously raise a queen bee colony and a worker honey bee colony.

Yet another objective is to allow for adjustments to the size of each bee compartment, so as to accommodate for population changes in the colonies.

Yet another objective is to generate electricity for bee keeping functions and sale to external energy markets.

Yet another objective is to help utility scale solar companies work around prohibitive regulations on farm land of class 1 and 2 soils by maintaining land in farm use and incentivizing the creation of pollination habitat.

Yet another objective is to solve the problem of caps on solar panel acreage imposed by government bureaucracy.

Yet another objective is to provide a hinged lid, carrying a solar panel, directly on the brooder box to allow access to bees inside.

Yet another objective is to provide multiple bee holes for bees to enter and exit each compartment of the brooder box.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIG. 4A shows a removable divider being moved to an opposite side of brooder box, and FIG. 4B shows the newly formed compartments resultant from moving the divider, in accordance with an embodiment of the present invention.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A photovoltaic horizontal beehive system 100 is referenced in FIGS. 1-5. The photovoltaic horizontal beehive system 100, hereafter "system 100", provides a unique horizontal beehive that serves the dual purpose of supporting a queen bee colony 122 and a worker honey bee colony 124 in separate, size adjustable compartments 108a-f; and further generates renewable energy to enhance the maintenance of the bees in the beehive, and export excess energy for external power needs. Thus, two objectives are achieved: 1) both queen bee and worker honey bee colonies are raised in the same brooder box 102; and 2) the brooder box 102 can be located remotely and have self-sufficient energy capacity.

Figure 1:
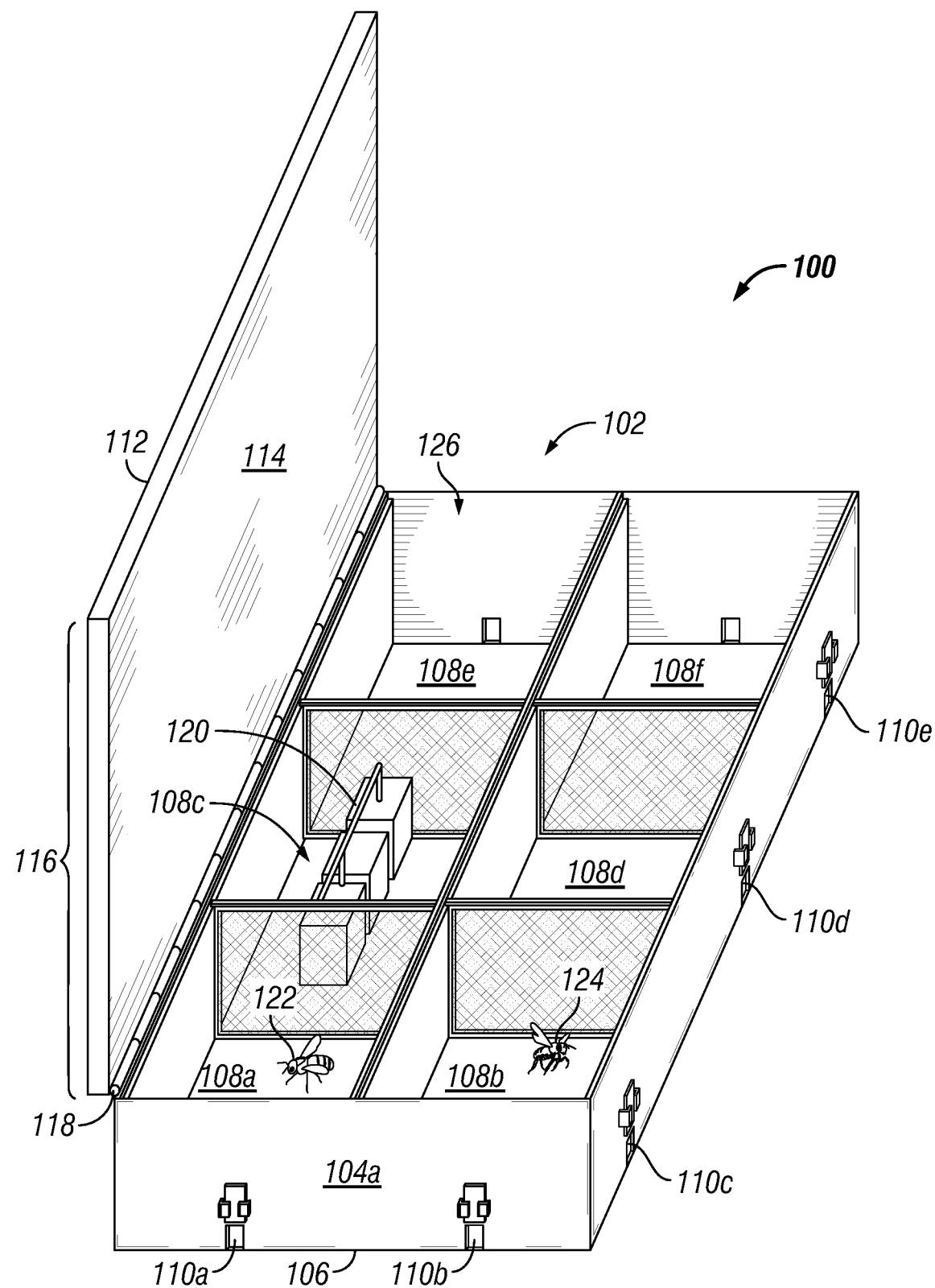
FIG. 1 illustrates a perspective view of an exemplary photovoltaic horizontal beehive system, showing a brooder box with the solar panel in an open position, in accordance with an embodiment of the present invention.

As referenced in FIG. 1, the system 100 comprises a brooder box 102, which serves as the housing where the eggs, larvae, and pupae of the bees develop. The brooder box 102 can support honeycomb cells that hold pollen, nectar, and honey. In essence, the brooder box 102 is where the bees live, work, and procreate. In one possible embodiment, the brooder box 102 comprises a horizontal beehive. Other types of beehives and man-made honey collection units known in the art may also be used. In addition, the brooder box 102 is compartmentalized, with at least one compartment 108a configured to hold a queen bee colony 122, at least one other compartment 108b, 108d, 108e, 108f configured to hold a worker honey bee colony 124, and at least one other compartment 108c configured to hold electrical components 120.

In one possible embodiment, the brooder box 102 is defined by a floor wall 106 and multiple sidewalls 104a-n that form an interior cavity 126. The sidewalls 104a-n may be elongated, so as to support a horizontal beehive configuration. In one non-limiting embodiment, four sidewalls form a rectangular arrangement for the brooder box 102. The floor wall 106 serves as the base for the brooder box 102, joining the sidewalls 104a-n in a perpendicular arrangement. In one alternative embodiment, a pallet 206 lies under the floor wall 106 to support the brooder box 102 for easy transport.

In some embodiments, the brooder box 102 is defined by a rectangular shape. In one non-limiting embodiment, the sidewalls 104a-n are about 65" long and 28" high. The system 100 is scalable, however, such that the brooder box 102 can be sized and dimensioned differently. Suitable materials for the brooder box 102 may include, without limitation, wood, plastic, rubber, aluminum, and metal alloys. Generally, the material allows the brooder box 102 to be sufficiently lightweight and portable.

Figure 2:
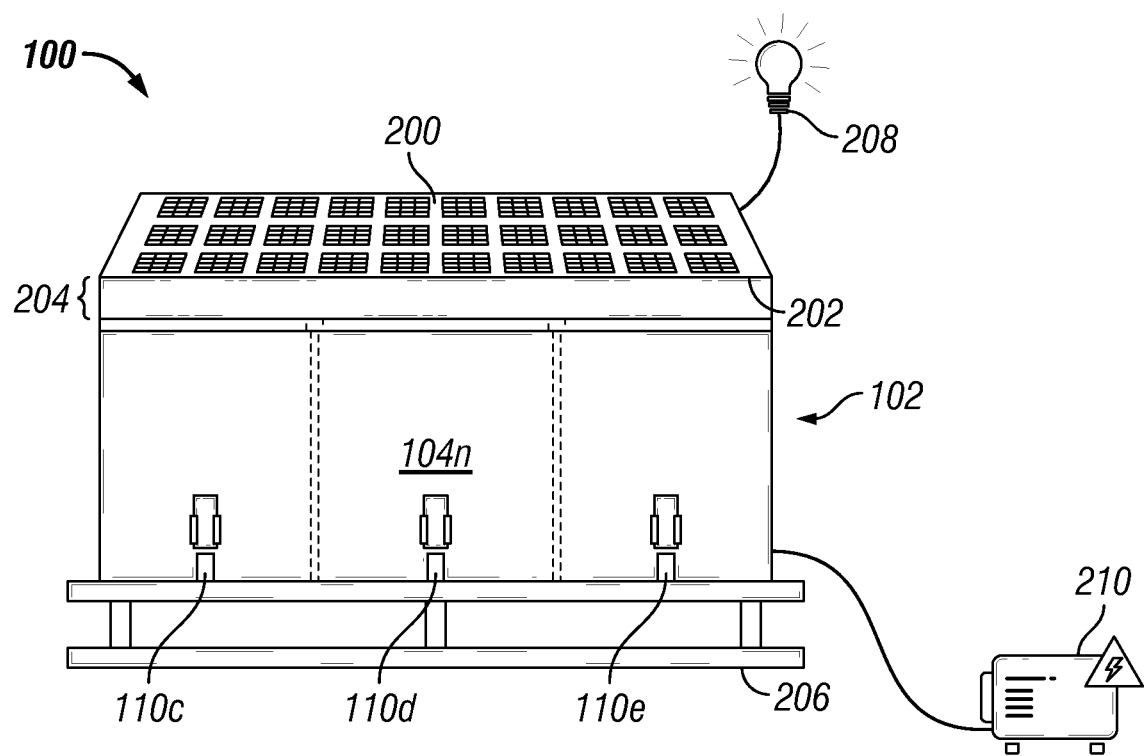
FIG. 2 illustrates a perspective view of the photovoltaic horizontal beehive system, showing the brooder box with the solar panel in a closed position, in accordance with an embodiment of the present invention.

The sidewalls 104a-n are defined by at least one bee passageway 110a-e at a bottom end of the sidewalls, near the floor wall 106 (See FIGS. 1-2). The bee passageway 110a-e is sized and dimensioned to enable passage between the interior cavity 126 and the exterior of the brooder box 102. Thus, the bees can easily ingress and egress the brooder box 102. This is especially helpful for the worker honey bees who collect pollen and returned to the brooder box 102 to deposit the pollen. The bee passageways 110a-e also serve to increase air circulation inside the brooder box 102.

Looking now at FIG. 2, the system 100 provides a lid 112 that is operable on the top edges of the sidewalls 104a-n for the brooder box 102. The lid 112 is a generally flat, rigid panel that is configured to move between an open position 116 and a closed position 204. In this manner, the lid 112 may regulate access to the interior cavity 126 of the brooder box 102. The lid 112 is defined by an outer surface 202 and an inner surface 114. The outer surface 202 orients outwardly to the exterior of the brooder box 102. As discussed below, a solar panel 200 fastens to the outer surface 202 in a parallel arrangement. Thus, the lid 112 also has a function of supporting electrical components 120 related to the solar panel 200.

In some embodiments, the lid 112 comprises a hinge 118, which allows the lid 112 to be hingedly attached to one of the sidewalls 104a-n of the brooder box 102. In this manner, the lid 112 pivotally articulates between the open and closed positions 116, 204. The hinged articulation of the lid 112 allows for easy access to the interior cavity 126, allowing a beekeeper to manipulate the lid 112 to the open position 116 (FIG. 1) for access to the bee colony; or to the closed position 204 (FIG. 2), so as to protect the electrical components 120 and the bee colonies 122, 124 from harsh external elements, i.e., weather, predators, excess sunlight. In other embodiments, the lid 112 can slide or simply detach from the sidewalls 104a-n to regulate access to the interior cavity 126.

In some embodiments, the system 100 further comprises a fixed central divider 300 disposed substantially parallel with the sidewalls 104a-n and perpendicular with the floor wall 106. The fixed central divider 300 extends across the interior cavity 126, bifurcating the interior cavity 126 to for at least two equal compartments in the interior cavity 126 of the brooder box 102. In one embodiment, the central divider extends through the longitudinal of the interior cavity 126. In other embodiments, the fixed central divider 300 traverses the short distance across the brooder box 102. In any case, the fixed central divider 300 is fixedly fastened to the sidewalls 104a-n and the floor wall 106 through various fastening means known in the art, including nails, bolts, adhesives, and fastening brackets.

As discussed above, the brooder box 102 has size adjustable compartments 108a-f adapted contain queen bee colonies 122, worker honey bee colonies 124, and electrical components 120. In some embodiments, the compartments 108a-f may include, without limitation, a queen bee colony compartment 108a, a honey bee colony compartment 108b, 108d, 108e, 108f, and an electrical component compartment 108c. In some embodiments, each compartment used to hold bees is in communication with a bee passageway 110a-e.

Figure 3:
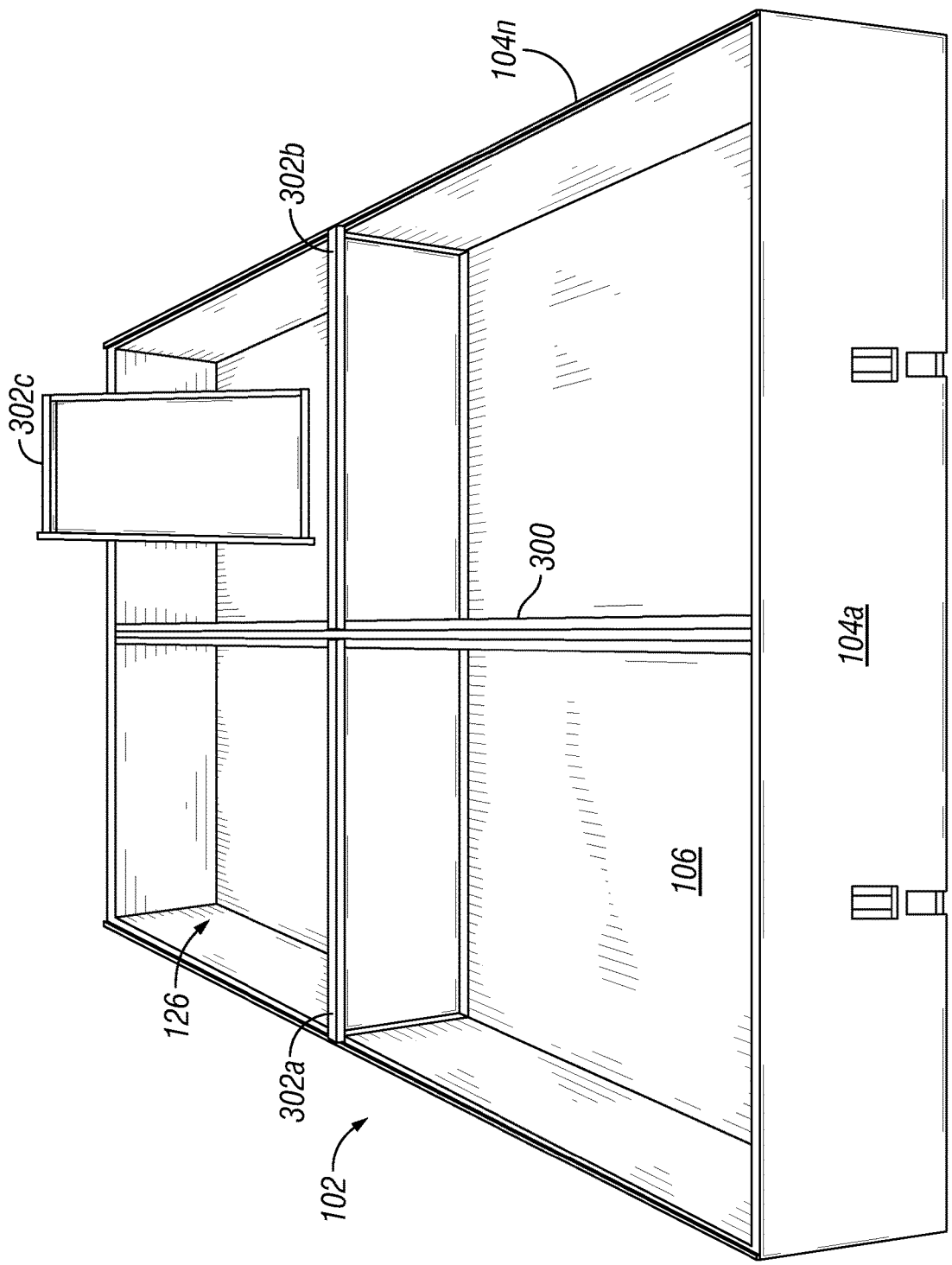
FIG. 3 illustrates a top isometric view of an exemplary brooder box segregated with a fixed divider and multiple removable dividers, in accordance with an embodiment of the present invention.

Turning now to FIG. 3, the segregated arrangement of the compartments 108a-f is possible through use of at least one removable divider 302a-d that serves to segregate the interior cavity 126 of the brooder box 102 into multiple compartments 108a-f. The removable divider 302a-d is disposed substantially parallel with the sidewalls 104a-n and perpendicular with the floor wall 106. In one non-limiting embodiment, the removable divider 302a-d is a flat panel that can be manipulated throughout the interior cavity 126 of the brooder box 102 to create differently sized compartments 108a-f.

Thus, the removable divider 302*a-d* is configured to reposition in the interior cavity 126. In some embodiments, the sidewalls 104*a-n* comprise an elongated slot, or a rail, for slidably guiding the removable divider to different sections of the interior cavity 126. The size and dimension of the compartments 108*a-f* is adjustable through manipulation of the removable dividers 302*a-d*. This allows for the formation of different numbers, sizes, and shapes of compartments 108*a-f* in the brooder box 102.

Figure 4A:
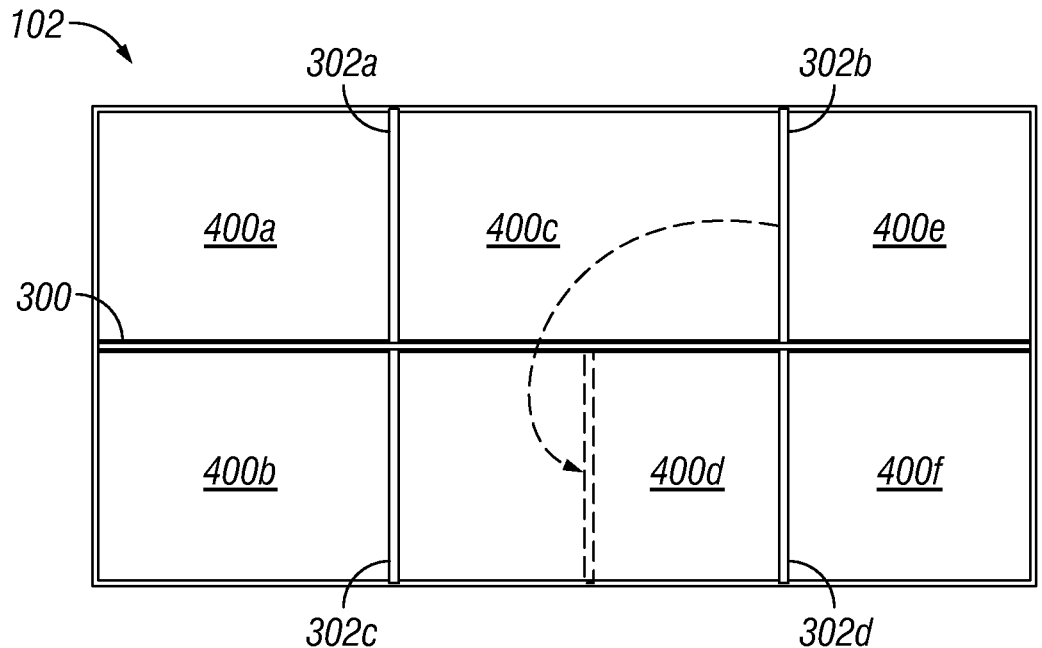
FIGS. 4A and 4B illustrate top views of the brooder box, where
Figure 4B:
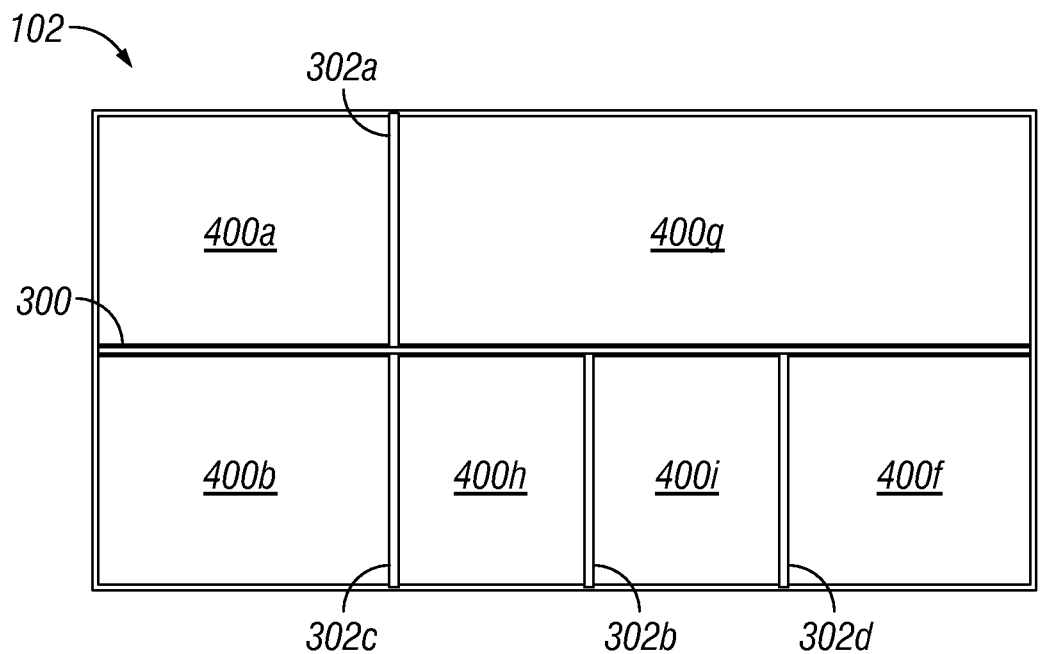

For example, FIGS. 4A-4B illustrate top views of the brooder box 102, where FIG. 4A shows a removable divider being moved to an opposite side of brooder box, and FIG. 4B shows the newly formed compartments resultant from moving the divider. As illustrated in FIG. 4A, a fixed central divider 300 extends longitudinally through the interior cavity 126. Four removable dividers 302*a*, 302*b*, 302*c*, 302*d* are fitted perpendicular to the fixed central divider 300 in an equal, spaced apart arrangement. This creates six equally sized, square or rectangular compartments 400*a*, 400*b*, 400*c*, 400*d*, 400*e*, 400*f*.

FIG. 4B, illustrates a first removable divider 302*b* being removed from one side of the fixed central divider 300 to the opposite side. The removal of removable divider 302*b* results in a new, larger compartment 400*g*. Adding the removable divider 302*b* to the opposite side of the fixed central divider 300 also works to create two smaller compartments 400*h*, 400*i*, to bifurcate compartment 400*d*. Though manipulation of the removable dividers, myriad mutations of compartments can be created to accommodate the bee colonies 122, 124, and the electrical components 120.

Through this quick, manual manipulation of the removable dividers, the interior cavity 126 is easily segregated into user-defined compartments; whereby the compartments are adjustable based on the size of a bee colony. For example, in the initial stages, the bee colony may be small, such that the entire bee colony is placed in a first compartment 108*a*, which is segregated from a second compartment 108*b* with the fixed central divider 300 and one or two removable dividers 302*a-d*. After some months, the one of the removable dividers 302*b* may be removed so that the first and second compartments 108*a-f* are combined to accommodate the larger bee colony. In one alternative embodiment, the fixed central divider 300 is installed during fabrication of the brooder box, while the removable dividers 302*a-d* are installed by the user, such as a beekeeper.

As illustrated in FIG. 2, a solar panel 200 is disposed on the outer surface 202 of the lid 112. The solar panel 200 may include a full photovoltaic cell that harnesses the power of the sun to generate direct current electricity. It is significant to note that the solar panel 200 generates electricity when the lid 112 is in both the open position 116 and the closed position 204. This source of renewable energy allows the system 100 to be operable in remote areas where electricity is not available. The generated electricity is used both internally in the brooder box 102, and transmitted externally for other operational uses.

Figure 5:
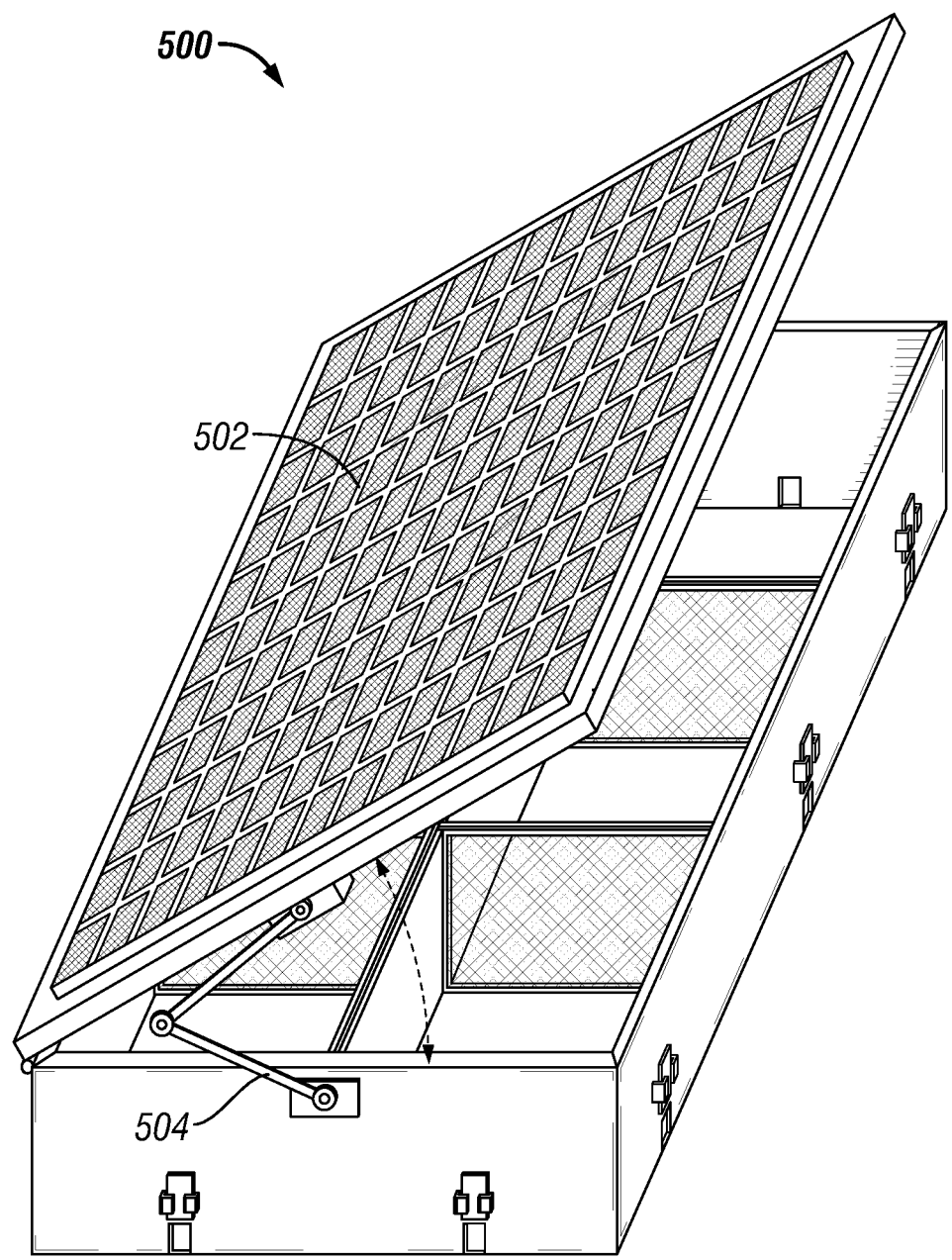
FIG. 5 illustrates an exemplary pivotable solar panel subassembly, showing the solar panel tilted at about 30° to optimize capture of the sunlight, in accordance with an embodiment of the present invention.

The system 100 is unique in that the capture of sunlight is optimized by controllably tilting the solar panel to follow the path of the sun. For example, FIG. 5 illustrates an exemplary pivotable solar panel subassembly 500, showing the solar panel 502 tilted at about 30° to optimize capture of the sunlight. An automated pivot hinge 504 may be used to carry the solar panel at the pivot trajectory, which is the full range of the sun's motion relative to the solar panel 502. In one non-limiting embodiment, the solar panel 502 pivots up to 180°.

In some embodiments, the automated pivot hinge 504 can be operatively connected to a small motor that carries the solar panel 502 and/or the lid 112 along the pivot trajectory. The pivotable solar panel subassembly 500 may also utilize a timer that controls the motor, actuating the motor in response to the path of the sun. This controlled pivotable relationship with the sun allows the system 100 to optimize the capture of the sun's energy, i.e., photons from both sides of the brooder box. It is significant to note that the pivotable solar panel subassembly 500 also takes advantage of the high albedo surface of the hive lid 112, i.e., white coloring to minimize reflectance of sunlight.

Looking again at FIG. 1, one or more electrical components 120 are disposed in an electrical component compartment 108*c*. The electrical components 120 are configured to regulate the generated electricity. This includes storage and voltage configuration of the electricity. In some embodiments, the electrical components 120 may include, without limitation, a battery, an inverter, a charge controller, and an electrical cable. In other embodiments, different types of electric components can be used, depending on the energy needs.

For example, the inverter is operatively connected to the solar panel 200, and operable to convert a direct current generated by the solar panel 200 to an alternating current. The charge controller is operatively connected to the solar panel 200, and operable to limit the rate of electrical current flowing from the solar panel 200. The electrical cable is operatively connected to the battery, and utilized to carry electricity externally and distantly from the brooder box 102.

As discussed above, the system 100 is helpful in rural areas, for when the electrical grid network is not accessible, for example solar panel bureaucratic codes or mountainous terrain may restrict the use of solar panels on a plot of farmland. Thus, as FIG. 1 shows, the brooder box 102 may contain an inverter that is operatively connected to the solar panel 200. The inverter is configured to change direct current generated by the solar panel 200 to alternating current.

The brooder box 102 may also contain a charge controller that is operatively connected to the solar panel 200. The charge controller limits the rate of current flowing from the solar panel 200. These electrical components are used when an external electrical grid network is not available for connecting to the solar panel. In yet other embodiments, the electrical components 120 include other electrical grid components, such as transformers, wires, and the like. Thus, as solar radiation is absorbed, the generated electricity is used for either, or internal beekeeping functions and selling to the external energy market. Furthermore, the present invention is differentiated from the prior art by producing surplus electricity for sale or use, and having the capacity to work around restrictive land use and bureaucratic regulations of solar energy.

Looking again at FIG. 2, the electricity generated by solar panel 200 is used to power an internal brooder box apparatus 208 that is located in, or proximal to the brooder box 102. In one possible embodiment, the internal brooder box apparatus 208 is a light source, a cooling component for cooling the interior cavity 126 of the brooder box 102, and an electrical mite exterminator. The light source can be useful for collecting honey or maintenance sing the brooder box 102 in darkness. The cooling component, such as a fan, can be useful for when the bees in the summer and removing harmful mites from the bee colonies. Other The generated electricity may be greater than the demands of the beehive; and therefore, surplus electricity is generated. This may be stored, or transmitted to an external energy market for sale. In this situation, the electricity powers an external electrical apparatus 210 that is disposed distally from the brooder box 102. The external electrical apparatus 210 may include an electrical fence, a data gathering device, and a generator. The external electrical apparatus 210 can be you useful for protecting the brooder box 102 from predators in remote, wilderness areas. The external electrical apparatus 210 can also be useful for powering devices that have no relation to the brooder box 102 or to the raising of bee colonies.

In operation, a beekeeper initiates honey production by starting a bee colony in a least one of the honeycomb compartments 108a-f. This may include coating a top bar of the removable dividers 302a-d with honey, or inserting a queen bee and a corresponding number of worker bees into the desired compartments 108a-f, which is segregated from other compartments 108a-f by the removable dividers 302a-d. The lid 112 is moved to the closed position 204, leaving the bees to ingress and egress freely through bee passageway 110a-es in the sidewall.

After a while, as the bee colony grows, the beekeeper may remove at least one of the removable dividers 302a-d to increase the size of the compartments 108a-f (See FIGS. 4A-4B). Furthermore, the solar panel 200 generates electricity by harnessing sunlight, and utilizing photovoltaic cells. The electricity may be stored in rechargeable batteries for use by beekeeping equipment or power tools, or transmitted to an external energy market for sale.

In conclusion, the system 100 provides a horizontal beehive. The brooder box 102 has sidewalls 104a-n and a floor wall 106 that form an interior cavity 126. The cavity 126 is segregated into independent compartments 108a-f through a central fixed divider, and multiple removable dividers 302a-d that segregate the brooder box 102 into a queen bee colony and a honey bee colony. The removable dividers 302a-d are manipulated in the cavity 126 to adjust the size of each compartment to accommodate population changes in the bee colonies.

Continuing, a lid 112 regulates access to the interior cavity 126. A solar panel 200 operates on outer surface 202 of lid 112. The solar panel 200 harnesses sunlight to generate electricity used internally and externally of the brooder box 102. An electrical compartment 120 in a component compartment 108c holds the electrical components 120, like a battery, an inverter, and a charge controller. The solar-generated electricity is used internally for operation of an internal beehive apparatus, and carried distally to operate an external electrical apparatus.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A photovoltaic horizontal beehive system, the system comprising:
   a brooder box having a floor wall and multiple sidewalls forming an interior cavity, the sidewalls being defined by at least one bee passageway enabling passage between the interior cavity and the exterior of the brooder box;
   a lid disposed on the sidewalls of the brooder box, the lid being operable to move between an open position and a closed position to regulate access to the interior cavity of the brooder box, the lid being defined by an outer surface and an inner surface;
   at least one removable divider operable to segregate the interior cavity of the brooder box into multiple compartments, the removable divider being disposed substantially parallel with the sidewalls and perpendicular with the floor wall, the removable divider further being operable to reposition in the interior cavity,
   whereby the size and dimension of the compartments is adjustable;
   a solar panel disposed on the outer surface of the lid, the solar panel is operable to pivot up to 180° about an automated pivot hinge to harness sunlight for generating electricity; and
   one or more electrical components operatively connected to the solar panel, the electrical components operable to regulate the generated electricity, the electrical components disposed in at least one of the compartments of the brooder box,
   whereby the electricity is regulated for powering an internal brooder box apparatus in, or proximal to the brooder box,
   whereby the electricity is regulated for powering an external electrical apparatus disposed distally from the brooder box.

2. The system of claim 1, wherein the brooder box is defined by a rectangular shape.

3. The system of claim 1, wherein the brooder box comprises a horizontal beehive.

4. The system of claim 1, wherein the sidewalls are about 65" long and 28" high.

5. The system of claim 1, further comprising a fixed central divider traversing centrally across the interior cavity of the brooder box, the fixed central divider operable to segregate the interior cavity of the brooder box.

6. The system of claim 1, wherein the sidewalls comprise a rail for slidably guiding the removable divider.

7. The system of claim 1, wherein the lid comprises a hinge.

8. The system of claim 7, wherein the lid is hingedly attached to one of the sidewalls of the brooder box.

9. The system of claim 1, wherein each compartment is in communication with a bee passageway.

10. The system of claim 1, wherein the compartments comprise a queen bee colony compartment, a honey bee colony compartment, and an electrical component compartment.

11. The system of claim 1, wherein the solar panel comprises multiple photovoltaic cells.

12. The system of claim 1, wherein the electrical components include at least one of the following: a battery, an inverter, a charge controller, and an electrical cable.

13. The system of claim 12, wherein the inverter is operatively connected to the solar panel, and operable to convert a direct current generated by the solar panel to an alternating current.

14. The system of claim 12, wherein the charge controller is operatively connected to the solar panel, and operable to limit the rate of electrical current flowing from the solar panel.

15. The system of claim 1, wherein the internal brooder box apparatus includes at least one of the following: a light source, a cooling component for cooling the interior cavity of the brooder box, and an electrical mite exterminator.

16. The system of claim 1, wherein the external electrical apparatus includes at least one of the following: an electrical fence, a data gathering device, and a generator.

17. A photovoltaic horizontal beehive system, the system comprising:
- a brooder box having a floor wall and multiple sidewalls forming an interior cavity, the sidewalls being defined by at least one bee passageway enabling passage between the interior cavity and the exterior of the brooder box;
- a lid disposed on the sidewalls of the brooder box, the lid being operable to move between an open position and a closed position to regulate access to the interior cavity of the brooder box, the lid being defined by an outer surface and an inner surface;
- a fixed central divider traversing centrally across the interior cavity of the brooder box, the fixed central divider operable to segregate the interior cavity of the brooder box;
- at least one removable divider operable to segregate the interior cavity of the brooder box into multiple compartments, the removable divider being disposed substantially parallel with the sidewalls and perpendicular with the floor wall, the removable divider further being operable to reposition in the interior cavity,
- whereby the size and dimension of the compartments is adjustable;
- a solar panel disposed on the outer surface of the lid, the solar panel is operable to pivot up to 180° about an automated pivot hinge to harness sunlight for generating electricity; and
- one or more electrical components operatively connected to the solar panel, the electrical components operable to regulate the generated electricity, the electrical components disposed in at least one of the compartments of the brooder box, the electrical components including at least one of the following: a battery, an inverter, a charge controller, and an electrical cable,
- whereby the electricity is regulated for powering an internal brooder box apparatus in, or proximal to the brooder box, the internal brooder box apparatus including at least one of the following: a light source, a cooling component for cooling the interior cavity of the brooder box, and an electrical mite exterminator,
- whereby the electricity is regulated for powering an external electrical apparatus disposed distally from the brooder box, the external electrical apparatus including at least one of the following: an electrical fence, a data gathering device, and a generator.

18. The system of claim 17, wherein the sidewalls comprise a rail for slidably guiding the removable divider.

19. A photovoltaic horizontal beehive system, the system comprising:
- a horizontal beehive having a floor wall and multiple sidewalls forming an interior cavity, the sidewalls being defined by at least one bee passageway enabling passage between the interior cavity and the exterior of the horizontal beehive, the sidewalls comprising a rail;
- a pallet disposed adjacent and parallel to the floor wall;
- a lid disposed on the sidewalls of the horizontal beehive, the lid being operable to move between an open position and a closed position to regulate access to the interior cavity of the horizontal beehive, the lid being defined by an outer surface and an inner surface;
- a fixed central divider traversing centrally across the interior cavity of the horizontal beehive, the fixed central divider operable to segregate the interior cavity of the horizontal beehive;
- at least one removable divider operable to segregate the interior cavity of the horizontal beehive into multiple compartments, the removable divider being disposed substantially parallel with the sidewalls and perpendicular with the floor wall, the removable divider further being operable to reposition in the interior cavity by sliding along the rail on the sidewalls,
- whereby the size and dimension of the compartments is adjustable;
- a solar panel disposed on the outer surface of the lid, the solar panel is operable to pivot up to 180° about an automated pivot hinge to harness sunlight for generating electricity; and
- one or more electrical components operatively connected to the solar panel, the electrical components operable to regulate the generated electricity, the electrical components disposed in at least one of the compartments of the horizontal beehive, the electrical components including at least one of the following: a battery, an inverter, a charge controller, and an electrical cable, the inverter being operatively connected to the solar panel, and operable to convert a direct current generated by the solar panel to an alternating current, the charge controller being operatively connected to the solar panel, and operable to limit the rate of electrical current flowing from the solar panel,
- whereby the electricity is regulated for powering an internal beehive apparatus in or proximal to the horizontal beehive, the internal beehive apparatus including at least one of the following: a light source, a cooling component for cooling the interior cavity of the horizontal beehive, and an electrical mite exterminator,
- whereby the electricity is regulated for powering an external electrical apparatus disposed distally from the horizontal beehive, the external electrical apparatus including at least one of the following: an electrical fence, a data gathering device, and a generator.

* * * * *